United States Patent [19]
Leban

[11] Patent Number: 5,108,109
[45] Date of Patent: Apr. 28, 1992

[54] BOARD GAME WITHOUT A BOARD

[76] Inventor: Bruce P. Leban, 11 Rose St., Somerville, Mass. 02143

[21] Appl. No.: 537,874

[22] Filed: Jun. 13, 1990

Related U.S. Application Data

[63] Continuation-in-part of Ser. No. 300,858, Jan. 24, 1989, abandoned.

[51] Int. Cl.⁵ .................................................. A63F 3/00
[52] U.S. Cl. .................................... 273/242; 273/258; 273/275
[58] Field of Search ............... 273/241, 242, 252, 258, 273/261, 263, 264, 268, 275, 276, 282, 283, 284, 287, 290

[56] References Cited

U.S. PATENT DOCUMENTS

| | | | |
|---|---|---|---|
| 259,217 | 6/1882 | Sanderson | 273/290 |
| 1,144,743 | 6/1915 | Upjohn | 273/258 |
| 2,162,876 | 6/1939 | Barton | 273/242 |
| 2,437,819 | 3/1948 | Heuser | 273/258 |
| 2,536,380 | 1/1951 | Lucassen | 273/242 |
| 2,571,195 | 10/1951 | Buck | 273/275 X |
| 2,585,268 | 2/1952 | Olsen | 273/258 |
| 2,703,713 | 3/1955 | Moyer | 273/290 X |
| 3,692,310 | 9/1972 | Martin | 273/241 |
| 3,741,545 | 6/1973 | Weisbecker | 273/258 |
| 3,820,791 | 6/1974 | Powers | 273/275 X |
| 3,863,929 | 2/1975 | Kahan | 273/275 |
| 4,025,076 | 5/1977 | Lipps | 273/294 |
| 4,436,309 | 3/1984 | Barlow | 273/275 X |
| 4,552,363 | 11/1985 | Rehkemper | 273/290 X |
| 4,674,753 | 6/1987 | Hochstim | 273/258 |
| 4,809,987 | 3/1989 | Dvorak | 273/290 X |

FOREIGN PATENT DOCUMENTS

| | | | |
|---|---|---|---|
| 2260365 | 9/1975 | France | 273/264 |
| 8803430 | 5/1988 | World Int. Prop. O. | 273/252 |

Primary Examiner—William H. Grieb
Assistant Examiner—William E. Stoll

[57] ABSTRACT

The invention consists of a game composed of a plurality of tiles which are arranged to form a playing surface, each tile divided into a plurality of subunits, each subunit having a plurality of distinguishing characteristics, a plurality of pawns which can occupy these subunits and can move on this surface. The players start the game by placing the tiles on a table and the pawns on the subunits to create an initial layout. Play then progresses with each play consisting of the movement of a tile to create a new layout or the movement of a pawn on the playing surface. The tiles may be arranged in an arbitrary manner subject to the constraint that the resulting configuration must always be connected and subunits on one tile must be aligned with subunits on adjacent tiles. A particular subconfiguration of pawns and tiles is designated as the goal and the player achieving this configuration wins the game. Another subconfiguration is defined which allows the player achieving that configuration to move one of the opposing player's pawns.

20 Claims, 3 Drawing Sheets

BOARD GAME WITHOUT A BOARD

This is a continuation-in-part of application Ser. No. 07/300,858 filed Jan. 24, 1989, now abandoned.

PRIOR ART AND BACKGROUND

This invention relates generally to board games and more specifically to abstract strategy games where players attempt to maneuver the playing pieces to a goal configuration.

The defining property of a board game is usually that it includes a board which serves as a playing surface with pieces moving on this surface.

A unique feature of the present invention is that the playing surface is not a stable configuration but rather is rearranged constantly during the play of the game.

Most board games have a playing surface which is fixed in shape and detail and games of this type clearly do not anticipate the present invention. The prior art includes a number of games which resemble the present invention superficially in that (1) tiles are arranged to form a playing surface or portion of a playing surface or (2) the game has a board which changes during play of the game.

The majority of games in the first group are distinguished from the present invention in most of the following respects: (i) the tiles are arranged in a particular fixed shape; (ii) the tiles are not rearranged during the play of the game; (iii) there is no interaction between the movement or placement of tiles and the movement or placement of other pieces; (iv) each tile represents a single playing position; and (v) the tiles require indicia to indicate their effect on the play of the game. Games in this group include Trippples (U.S. Pat. No. 3,820,791) and the game described in Schifman U.S. Pat. No. 3,989,253.

The majority of games in the second group are distinguished from the present invention in most of the following respects: (i) the board is composed of pieces which may be rotated, slid back and forth or otherwise repositioned in a constrained manner; (ii) pieces of the board maintain their relative positions; (iii) there is a distinguished initial configuration; (iv) there are relatively few (less than one million) possible configurations; and (v) these games are race or maze games or variations of common games such as chess and checkers. Games in this group include Shuttles (Shoptaugh U.S. Pat. No. 3,731,934) and the game apparatus described in Escamilla-Kelly U.S. Pat. No. 4,348,027.

The present invention falls into both groups and is clearly not anticipated by the previously described games. There are also a few games in the prior art which fall into both groups. These all differ from the present invention in other important respects.

The game Octiles (Dale Walton) uses tiles which are positioned to form paths of a playing surface. This game differs from the present invention in at least these respects: (i) the tiles are arranged in a particular fixed shape on a board; (ii) the tiles represent the connections between the playing positions rather than the playing positions themselves; (iii) the tiles require indicia to indicate their effect on the play of the game; and (iv) the game is a race game.

The game Proteus (Michael Waitsman) uses tiles which trade positions and turn over. This game differs from the present invention in at least these respects: (i) the tiles are arranged in a particular fixed shape on a board; (ii) each tile represents a single playing position; (iii) the movement of the pawns is according to chess-like rules rather than depending on the placement of the tiles (the particular rules in effect depends on which tiles are face up, but not on their positions); and (iv) the tiles require indicia to indicate their effect on the play of the game.

SUMMARY OF THE INVENTION

The object of the present invention is not to correct a perceived deficiency in existing board games since people have been enjoyably playing games like chess for thousands of years. Instead, the object is to create a new and different game which is esthetically satisfying and enjoyable to play.

Another object of the present invention is to create a game which lies outside the traditional perception of what a board game is, but at the same time is instantly recognizable as a type of board game: in this case, a board game without a board.

Another object is to create a game in which the rules of the game can be naturally embodied in the game apparatus rather than requiring indicia on the game pieces (as is the case with many games in the prior art). This would make the rules easy to remember. For example, the goal configuration is represented in the preferred embodiment by a unique tile which represents that configuration.

Another object is to create a game where play must take place on more than one conceptual level. In playing the preferred embodiment, players must simultaneously contemplate the movement of the tiles and the movement of the pawns. A related object is that all types of moves available to the players should interact with the other types of moves available.

Other objects will be apparent from reading the description of the preferred embodiment and the claims.

The present invention, in summary, consists of a game where a plurality of tiles are arranged to form a playing surface. Players rearrange the tiles to change the playing surface and move pawns on this surface. A player achieving a defined goal configuration wins.

BRIEF DESCRIPTION OF THE DRAWINGS

The invention itself is set forth in the claims. The drawings illustrate the preferred embodiment of the invention as described below:

DESCRIPTION OF THE PREFERRED EMBODIMENT

An embodiment of the invention is to be marketed under the trade name Fractiles and it is essentially this embodiment which is described here. The description of this embodiment includes specific numbers in reference to the game and its apparatus. This should not be construed to limit the invention as set forth in the claims. The use of the specific numbers is merely a matter of convenience in understanding the preferred embodiment. In some cases, reference is made to alternate embodiments of the invention to clarify the distinction between elements of the preferred embodiment and the present invention.

Figure 1:
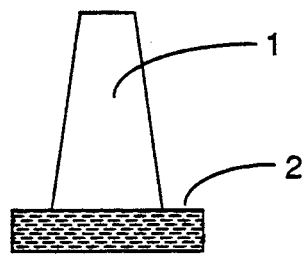
FIG. 1 is a side view of one of the pawns used in the game.

FIG. 1 shows the pieces of game apparatus called pawns 1. Each player has three pawns which are distinguished in some manner from that of the opposing player. In the preferred embodiment, pawns of one player are blue and the pawns of the opposing player are red. Each pawn is coded to match the subunits it is permitted to occupy. In the preferred embodiment, the base 2 of each pawn is color-coded to match the colors of the tile subunits (all pawns are restricted to subunits of a single color and otherwise move identically). It should be noted that several words "pawn," "token," and "man" are all generically used in the game art for playing pieces that move on a playing surface. The word "pawn" is chosen because it is more common than "token" and preferred over "man" and that this usage has no relation to pawns in other games (e.g., chess) nor does it exclude the possibility of more than one variety of pawn.

Figure 2:
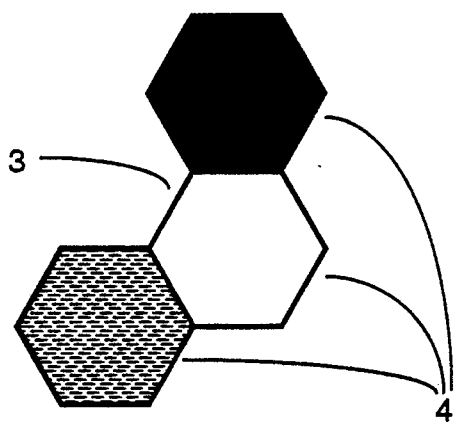
FIG. 2 is a plan view of one of the game tiles.

FIG. 2 shows a piece of game apparatus called a tile. Each tile 4 has a plurality of subdividing means which subdivide the tile into subunits 5, each subunit having a plurality of distinguishing means. Each subunit is capable of having a plurality of pawns positioned on it. In the preferred embodiment, the subunits are identically hexagonally shaped and the subunits on a given tile are uniquely distinguished by their color, one subunit on each tile being white, gray and black. As illustrated, the subdividing means comprises three separate subunit components affixed to a base. Other subdividing means are possible. For example, an alternate embodiment has an affixed central subunit which has the effect of dividing the base into two additional subunits.

An alternate embodiment could have each subunit have more than one distinguishing means. For example, each subunit could also have stripes running in a particular direction and subunits would be considered similar if they have parallel stripes. Note that in such an embodiment, rotating a tile would have the effect of changing the interpretation of the distinguishing means of each subunit. It should be noted that normally in the game art, the word "space" or "square" would be used instead of "subunit." However, "space" is avoided because it apparently has a standard conflicting meaning in the patent literature (namely "gap") and "square" would be confusing since the preferred embodiment uses hexagons. Additionally, the use of the word "tile" is not standardized. The word "tile" is used in the game art to refer both to pieces played on a playing surface (e.g., Scrabble) and to pieces used to form a playing surface, with or without a board. Only the latter meaning is intended here.

In the preferred embodiment, there are twelve tiles of the same shape and general features as 4 except that the tiles vary in their combination of distinguishing means. There are six possible permutations of three elements and the preferred embodiment includes two of each such tile. The tiles are composed of any suitable rigid material, such as wood, plastic, ceramic or metal. The use of color as a distinguishing means, as in the preferred embodiment, should not be used to dismiss the concept of a distinguishing means as trivial. Consider that Chess usually distinguishes the pieces of the two players by color, yet it can hardly be considered trivial that the pieces of the two players can be distinguished from each other. The presence of some distinguishing means is an essential component of the game.

The term "distinguishing means" does not mean "indicia." A distinguishing means of a set of objects is a feature of some of the objects which is not shared by all the objects. Shape, color and size are the most commonly used distinguishing means. Texture is used as a distinguishing means in games adapted for blind players. Frequently, many objects share one distinguishing means while differing in another.

One distinguishing means can be easily replaced by another. For example, chess sets are frequently made in colors other than black and white. Additionally, the shapes of the pieces in chess are distinguishing means because they have no intrinsic meaning. Chess sets are frequently made which use entirely different shapes for the pieces (e.g., historical figures).

On the other hand, indicia are not interchangeable, since the mark itself has meaning. For example, note that the arrows on the tiles in Trippples, the paths on the tiles in Octiles and the prices printed on a Monopoly board could not be easily replaced by other indicia.

Figure 3:
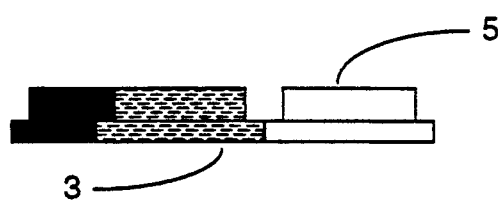
FIG. 3 is a side view of one of the game tiles.

FIG. 3 shows a side view of a tile. The raised portion of each tile 6 is designed to allow a player to easily pick a tile up even if it is completely surrounded by other tiles.

Figure 4:
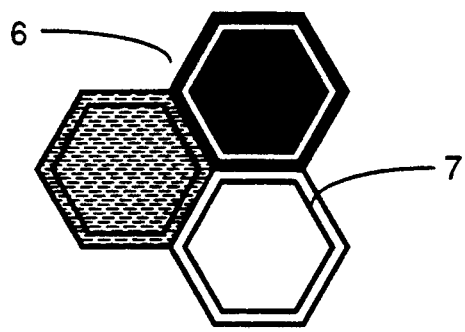
FIG. 4 is a plan view of the tile designated as the goal tile.

FIG. 4 shows an additional thirteenth tile 7 which can be distinguished by its shape. For convenience, in plan views, this tile is also identified by the distinguishing marks 8. Note that these marks do not constitute indicia. This tile is designated as the goal tile and a player wins by maneuvering three pawns onto the three subunits 9.

Play of the game is in three phases. The first phase consists of arranging the tiles to form a playing surface. The second phase consists of placing the pawns on this surface in an initial configuration. The third phase consists of moving the tiles and pawns in an attempt to achieve the goal configuration. One player moves first in the first and second phases and the other player moves first in the third phase.

The first phase starts with the goal tile 7 placed in the center of the table. The first player then places one of the other tiles 4 on the table in such a manner that it shares at least one edge with at least one of the previously placed tiles and the players alternate doing this until all tiles have been placed.

Figure 5:
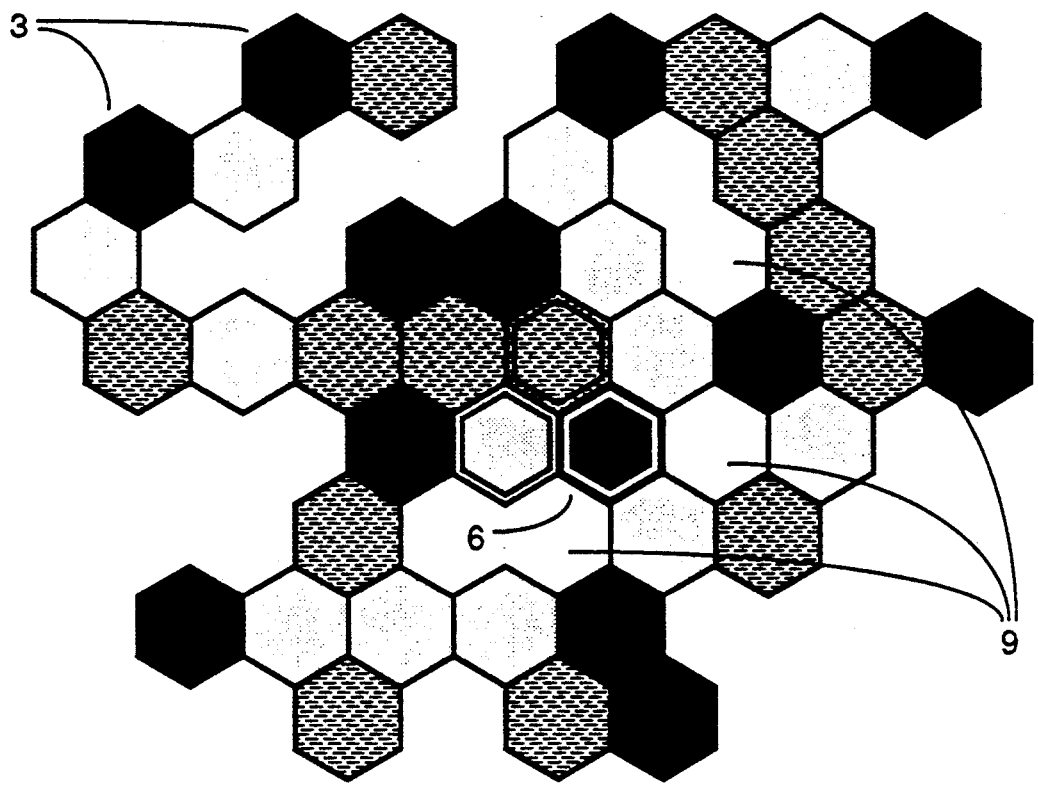
FIG. 5 is a plan view of a possible configuration at the end of the first phase of the game.

FIG. 5 shows a possible game configuration at the end of the first phase. Notice that at the completion of the first phase, the playing surface may be of arbitrary shape and may surround holes or gaps 10. Unlike most games, the present invention imposes no external limitation on the shape of the layout other than physical constraints of the tiles (e.g., tiles may not occupy the same physical space).

The second phase proceeds with each player placing the other player's pawns on the playing surface. The first player places one of the second player's pawns 1 on one of the subunits on the playing surface and the players then alternate placing pawns until all pawns have been placed. One pawn of each player must be on a subunit of each color. In an alternate embodiment, the details of this phase would clearly depend on the distinguishing means chosen for the subunits.

The third phase proceeds with each player alternately making a move. If when it is one of the player's turn to move, that player has no available moves then the game is a draw. A move consists of one of the players moving either a pawn or a tile. The player must choose one of the two kinds of move to make at each turn. If players were allowed to make both kinds of moves at a single turn, then, on every turn, they could either advance a pawn or make both an offensive and defensive move. This would reduce the game to a race game.

A pawn may move from the subunit it occupies to any other unoccupied subunit of the same color provided that there is an uninterrupted straight line of unoccupied subunits connecting the originating subunit and the terminating subunit in one of the six normal directions for a hexagonal grid. In an alternate embodiment using rectangular subunits, movement could be allowed in the four normal directions, the four diagonal directions or all eight directions.

Figure 6:
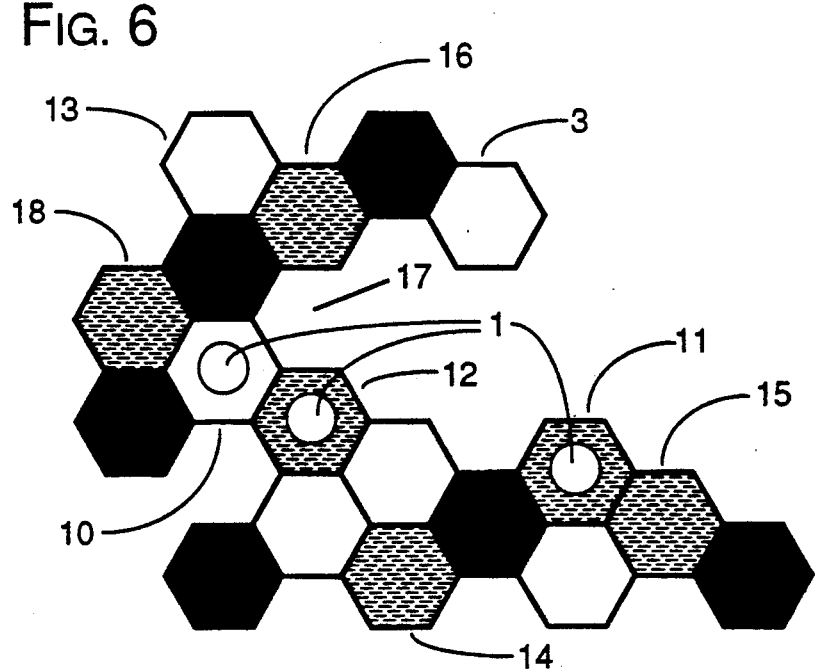
FIG. 6 is a plan view of a section of a game configuration for illustration of pawn moves.

FIG. 6 shows a plan view of a section of a game configuration. Pawns 1 are shown as occupying subunits 11, 12 and 13. The pawn on subunit 11 can move to subunit 14 and the pawn on subunit 12 can move to subunits 15 and 16. In contrast, The pawn on subunit 13 would be unable to move. In particular, it cannot move to subunit 15 because it is not in one of the six normal directions, it cannot move to subunit 17 because there is a gap 18 in the line of subunits, and it cannot move to subunit 19 because there is an occupied subunit 11 in the line of subunits.

If after a player makes a move, the player has formed a triangle of three mutually adjacent subunits which are occupied by two of that player's pawns (one of these just having been moved) and one of the opposing player's pawns, the moving player is entitled to move one of the opposing player's pawns to any other unoccupied subunit of any tile comprising the playing surface of the appropriate color. This is referred to as "bumping."

Figure 7:
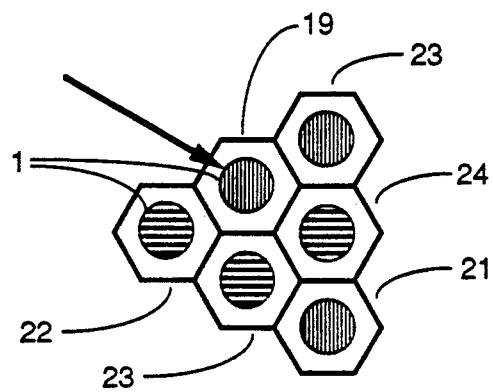
FIG. 7 is a plan view of a section of a game configuration for illustration of bumping.

FIG. 7 shows a plan view of a section of a game configuration. The colors of the subunits have not been indicated since that is irrelevant to the discussion. The pawns 1 shown occupying subunits 20, 21 and 22 are one player's and the pawns shown occupying subunits 23, 24 and 25 are the opposing player's. Assuming that the pawn on subunit 20 had just moved to this position as indicated by the arrow, this pawn along with the pawn on subunit 21 would allow the player who moved the pawn to bump the pawn occupying subunit 25. Note that neither of the pawns occupying subunits 20 and 22 is bumped. In order for a player to be entitled to make a bump, the player must make a move which forms a triangle as described above.

A tile may be moved from the position it occupies to a new position provided that it is unoccupied, it is not the goal tile, and if the immediate previous move was a tile move, it is not the same tile. A tile may be moved to occupy a new position provided that the resulting configuration is flat and connected, that any two tiles which touch share at least one edge and if the immediate previous move was a tile move, the tile moved on this turn must not be moved to a position identical to that originally occupied by the tile moved on the previous move. The last two conditions on each tile move are intended to prevent one move from nullifying the effect of the immediate previous move. If one player can move the same tile as just moved or move another tile into the same position, the game can degenerate into players moving the same few tiles back and forth.

Figure 8:
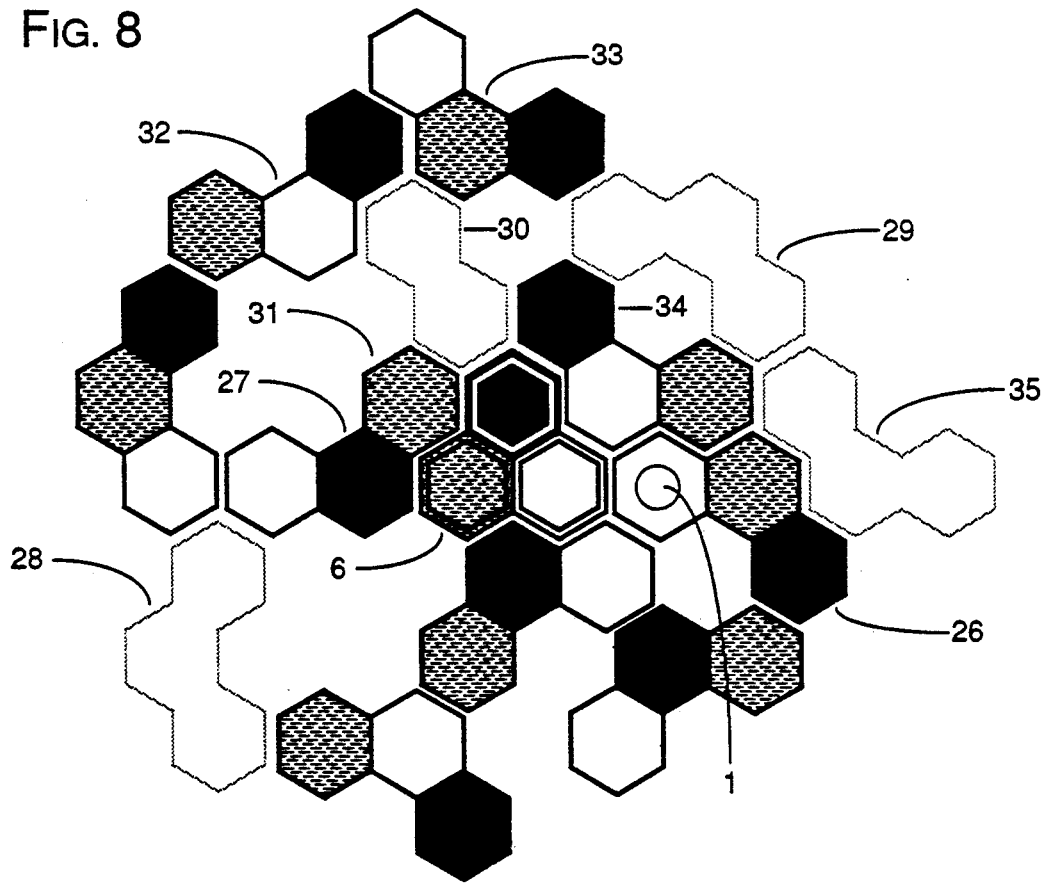
FIG. 8 is a plan view of a section of a game configuration with gaps left between the tiles for illustration of tile moves.

FIG. 8 shows a plan view of a section of a game configuration. Gaps have been shown between the tiles for illustrative purposes. The tile 27 cannot be moved because it is occupied by the pawn 1. The tile 7 cannot be moved because it is the goal tile. The tile 28 can be moved to a number of new positions, including those illustrated by the outlines 29 and 30. It can also be moved to occupy the position illustrated by the outline 31, overlapping its previous position at subunit 32. Tile 27 can be placed in exactly one way to occupy the outline 31 because the tile is rotationally asymmetric and placing the tile in any other orientation would overlap another tile at one of the subunits 32, 34 or 35. The tile 27 cannot be moved to the position illustrated by the outline 36 because doing so would disconnect the playing surface into two parts.

To clarify the distinction between rotationally symmetric and asymmetric, consider the the goal tile 7, a domino and tile 27. The first two items are rotationally symmetric and the latter is rotationally asymmetric. If the goal tile or a domino is removed from a layout it can be replaced to occupy the same physical space in more than one way. In contrast, if tile 27 is removed from a layout it can only be replaced to occupy the same physical space in exactly one way. If a tile does not have subunits or indicia, the concept of rotational symmetry is usually irrelevant: any placement of the tile which occupies the same physical space is functionally identical. A double domino (two of the same number) is rotationally symmetric, but the two placements of the domino cannot be distinguished. Rotational asymmetry is important in the present invention because it places a physical limitation on how the tiles may be arranged. It is not always possible to remove a tile and replace it in a desired way.

The game as described above is one embodiment of the invention. It is contemplated that other variations may be made, including variations in the types and numbers of the subunits, in the tiles and subunits on each tile including a plurality of differently shaped subunits or tiles in a single game and including the use of subunits or tiles suitably shaped to force the presence of holes in the playing surface such as pentagons, or irregularly shaped tiles and tiles which fit together to form a three-dimensional or non-planar playing surface, in the number of distinguishing means present on each subunit and the combinations of such means, in the types and number of pawns, in the number of players, in the order of play, and in the precise rules governing movement. It is also contemplated that variations in the physical components of the game may be made, including a computer version of the game which simulates the physical components using the input and output devices of the computer, drawing a graphic representation of the components on the screen and allowing the components to be manipulated with the keyboard or mouse. It is intended that the claims below cover all such variations of the game.

I claim:

1. A method of playing a game using apparatus comprising:
   a plurality of playing pieces,
   said pieces comprising a plurality of pawns and a plurality of tiles, said tiles being adapted for random layout relative to any of the others of said tiles so that they can form a playing surface of undetermined shape prior to the commencement of the game and being adapted so that, during a game, a tile can be removed from the layout and replaced in another position to create a new layout of said playing surface, each said tile being subdivided into a plurality of areas, each such area being visually distinguishable, the areas being thus divided into groups, all the areas in each group being thus visually identical, one set of pawns for each player, each pawn being visually similar to the other pawns for that player and being visually distinct from the pawns for opposing players, one such tile designated as the goal tile, there being the same number of pawns for each player as areas of the goal tile, each pawn further having an attached subpart that is visually similar to one of the areas of the goal tile, said method comprising:

(1) a plurality of turns comprising:
  (a) a plurality of tile placement actions, where the player selects a tile from the set of tiles that have not yet been used during the game and places said tile so that, together with the tiles already placed, it forms a playing surface of undetermined shape prior to the commencement of the game,
  (b) a plurality of pawn placement actions, where the player selects a pawn from the set of pawns that have not yet been used during the game and positions said pawn on an area of the playing surface,
  (c) a plurality of tile movement actions, where the player removes a tile from the playing surface and replaces it in another position, and
  (d) a plurality of pawn movement actions, where the player removes a pawn from the area of the playing surface on which it is positioned and repositions the pawn on another area; and (2) a player is declared the winner when, after a player has completed a turn, the configuration of the pieces is such that all of the player's pawns are positioned on areas of the goal tile.

2. The method of playing a game of claim 1 where said tiles and areas are such that when the tiles are arranged to form a playing surface, areas on adjacent tiles may adjoin each other and such that it is possible to form configurations of three areas each of which adjoins the other two, said method further comprising:

when, after a player has completed a turn by repositioning a pawn, the configuration of the pieces is such that there are three areas each of which adjoins the other two, all of which have pawns positioned upon them, one of said pawns being the pawn just repositioned, the second of said pawns being a pawn of the player having just completed a turn and the third of said pawns being of an opposing player, the player having just completed a turn then removes the third of said pawns from the playing surface and repositions it on another area.

3. The method of playing a game of claim 2 further comprising:

when players are making pawn placement actions each player's pawns are placed by an opposing player.

4. The method of playing a game of claim 3 further comprising:

when a pawn is repositioned it may only be repositioned on an area that is a member of the same distinct area group as the area it was on before it was repositioned.

5. The method of playing a game of claim 3 where the areas are polygonal in shape and the method further comprises:

when a pawn is repositioned it must be repositioned on an area that lies in a direction perpendicular to one of the edges of the area it was on before it was repositioned and there must be a connected set of areas along the line of the direction of movement between the originating and terminating areas, none of said intervening areas having pawns positioned on them.

6. The method of playing a game of claim 3 where the areas are polygonal in shape and the method further comprises:

when a pawn is repositioned it may only be repositioned on an area that is a member of the same distinct area group as the area it was on before it was repositioned;

when a pawn is repositioned it must be repositioned on an area that lies in a direction perpendicular to one of the edges of the area it was on before it was repositioned and there must be a connected set of areas along the line of the direction of movement between the originating and terminating areas, none of said intervening areas having pawns positioned on them;

when a tile is placed or replaced it must be placed in a way that will keep the playing layout connected; and a tile that has pawns positioned on any of its areas may not be removed and replaced in another position.

7. The method of playing a game of claim 1 further comprising:

when players are making pawn placement actions each player's pawns are placed by an opposing player.

8. The method of playing a game of claim 1 further comprising:

when a pawn is repositioned it may only be repositioned on an area that is a member of the same distinct area group as the area it was on before it was repositioned.

9. The method of playing a game of claim 1 where the areas are polygonal in shape and the method further comprises:

when a pawn is repositioned it must be repositioned on an area that lies in a direction perpendicular to one of the edges of the area it was on before it was repositioned and there must be a connected set of areas along the line of the direction of movement between the originating and terminating areas, none of said intervening areas having pawns positioned on them.

10. The method of playing a game of claim 1 further comprising:

when a tile is placed or replaced it must be placed in a way that will keep the playing layout connected.

11. The method of playing a game of claim 1 further comprising:

a tile that has pawns positioned on any of its areas may not be removed and replaced in another position.

12. A method of playing a game using apparatus comprising:

a plurality of playing pieces, said pieces comprising a plurality of pawns and a plurality of tiles, said tiles being adapted for random layout relative to any of the others of said tiles so that they can form a playing surface of undetermined shape prior to the commencement of the game and being adapted so that, during a game, a tile can be removed from the layout and replaced in another position to create a new layout of said playing surface, each said tile being subdivided into a plurality of areas, each such area being visually distinguishable, the areas being thus divided into groups, all the areas in each group being thus visually identical, said tiles and areas being such that when the tiles are arranged to form a playing surface, areas on adjacent tiles may adjoin each other and such that it is possible to form configurations of three areas each of which adjoins the other two, one set of pawns for each player, each pawn being visually similar to the other pawns for that player and being visually distinct from the pawns for opposing players, said method comprising:
 (1) a plurality of turns comprising:
  (a) a plurality of tile placement actions, where the player selects a tile from the set of tiles that have not yet been used during the game and places said tile so that, together with the tiles already placed, it forms a playing surface of undetermined shape prior to the commencement of the game
  (b) a plurality of pawn placement actions, where the player selects a pawn from the set of pawns that have not yet been used during the game and positions said pawn on an area of the playing surface,
  (c) a plurality of tile movement actions, where the player removes a tile from the playing surface and replaces it in another position, and
  (d) a plurality of pawn movement actions, where the player removes a pawn from the area of the playing surface on which it is positioned and repositions the pawn on another area;
 (2) said turns being made by the players in the following sequence:
  (a) players alternately making tile placement actions until all tiles have been placed,
  (b) players alternately making pawn placement actions until all pawns have been placed,
  (c) players alternately choosing either (1) to make a turn comprising a tile movement action or (2) to make a turn comprising a pawn movement action, said tile movement actions and pawn movement actions interspersed in any order chosen by the players; and
 (3) when, after a player has completed a turn by repositioning a pawn, the configuration of the pieces is such that there are three areas each of which adjoins the other two, all of which have pawns positioned upon them, one of said pawns being the pawn just repositioned, the second of said pawns being a pawn of the player having just completed a turn and the third of said pawns being of an opposing player, the player having just completed a turn then removes the third of said pawns from the playing surface and repositions it on another area.

13. The method of playing a game of claim 12 further comprising:

when players are making pawn placement actions each player's pawns are placed by an opposing player.

14. The method of playing a game of claim 12 further comprising:

when a pawn is repositioned it may only be repositioned on an area that is a member of the same distinct area group as the area it was on before it was repositioned.

15. The method of playing a game of claim 12 where the areas are polygonal in shape and the method further comprises:

when a pawn is repositioned it must be repositioned on an area that lies in a direction perpendicular to one of the edges of the area it was on before it was repositioned and there must be a connected set of areas along the line of the direction of movement between the originating and terminating areas, none of said intervening areas having pawns positioned on them.

16. The method of playing a game of claim 12 further comprising:

when a tile is placed or replaced it must be placed in a way that will keep the playing layout connected.

17. A method of playing a game using apparatus comprising:

a plurality of playing pieces, said pieces comprising a plurality of pawns and a plurality of tiles, said tiles being adapted for random layout relative to any of the others of said tiles so that they can form a playing surface of undetermined shape prior to the commencement of the game and being adapted so that, during a game, a tile can be removed from the layout and replaced in another position to create a new layout of said playing surface, each said tile being subdivided into a plurality of areas, each such area being visually distinguishable, the areas being thus divided into groups, all the areas in each group being thus visually identical, one set of pawns for each player, each pawn being visually similar to the other pawns for that player and being visually distinct from the pawns for opposing players, said method comprising:
 (1) a plurality of turns comprising:
  (a) a plurality of tile placement actions, where the player selects a tile from the set of tiles that have not yet been used during the game and places said tile so that, together with the tiles already placed, it forms a playing surface of undetermined shape prior to the commencement of the game
  (b) a plurality of pawn placement actions, where the player selects a pawn from the set of pawns that have not yet been used during the game and positions said pawn on an area of the playing surface, (c) a plurality of tile movement actions, where the player removes a tile from the playing surface and replaces it in another position, and (d) a plurality of pawn movement actions, where the player removes a pawn from the area of the playing surface on which it is positioned and repositions the pawn on another area;

(2) said turns being made by the players in the following sequence:

(a) players alternately making tile placement actions until all tiles have been placed, (b) players alternately making pawn placement actions until all pawns have been placed, (c) players alternately choosing either (1) to make a turn comprising a tile movement action or (2) to make a turn comprising a pawn movement action, said tile movement actions and pawn movement actions interspersed in any order chosen by the players; and (3) when players are making pawn placement actions in step (2) (b) each player's pawns are placed by an opposing player.

18. The method of playing a game of claim 17 further comprising:

when a pawn is repositioned it may only be repositioned on an area that is a member of the same distinct area group as the area it was on before it was repositioned.

19. The method of playing a game of claim 17 where the areas are polygonal in shape and the method further comprises:

when a pawn is repositioned it must be repositioned on an area that lies in a direction perpendicular to one of the edges of the area it was on before it was repositioned and there must be a connected set of areas along the line of the direction of movement between the originating and terminating areas, none of said intervening areas having pawns positioned on them.

20. The method of playing a game of claim 17 further comprising:

when a tile is placed or replaced it must be placed in a way that will keep the playing layout connected.

* * * * *